United States Patent
Kataoka et al.

(12) 
(10) Patent No.: US 6,496,009 B2
(45) Date of Patent: Dec. 17, 2002

(54) GAS CONCENTRATION DETECTOR USING OXIDE-SEMICONDUCTOR

(75) Inventors: Hiroshi Kataoka, Kariya (JP); Yuji Honda, Okazaki (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/740,366

(22) Filed: Dec. 19, 2000

(65) Prior Publication Data

US 2001/0008374 A1 Jul. 19, 2001

(30) Foreign Application Priority Data

Jan. 18, 2000 (JP) ........................................ 2000-008737

(51) Int. Cl.⁷ .......................... G01N 27/62; G01R 27/08
(52) U.S. Cl. ...................... 324/464; 324/691; 324/713
(58) Field of Search ............................... 324/464–468, 324/713, 691; 374/141

(56) References Cited

U.S. PATENT DOCUMENTS 4,458,583 A 7/1984 Fukui
4,478,049 A * 10/1984 Fukui et al. .................. 62/179

FOREIGN PATENT DOCUMENTS

JP 11-240323 * 9/1999

* cited by examiner

Primary Examiner—Michael Sherry
Assistant Examiner—Paresh Patel
(74) Attorney, Agent, or Firm—Harness, Dickey & Pierce, PLC

(57) ABSTRACT

A gas concentration detector for detecting a concentration of pollutant gas such as NOx or SOx contained in ambient air is composed of an oxide-semiconductor gas sensor heated by a heater and a controller for determining the gas concentration by comparing a concentration level detected by the gas sensor with a calculated comparison level. The comparison level is calculated so that it follows the detected level with a certain delay. The degree of the delay is set shorter in an unstable region- of the gas sensor than in a stable region, thereby to effectively determine the gas concentration even in the unstable region.

12 Claims, 6 Drawing Sheets

GAS CONCENTRATION DETECTOR USING OXIDE-SEMICONDUCTOR

CROSS-REFERENCE TO RELATED APPLICATION

This application is based upon and claims benefit of priority of Japanese Patent Application No. 2000-8737 filed on Jan. 18, 2000, the content of which is incorporated herein by reference.

BACKGROUND OF THE INVENTION

1. Field of the Invention

The present invention relates to a detector for detecting a concentration of pollutant gas such as NOx using an oxide-semiconductor.

2. Description of Related Art

A gas concentration detector of this kind is disclosed in JP-A-11-240323. In this detector, a detected concentration level is compared with a calculated comparison level, and it is determined that a gas concentration is high when the ratio of the detected level to the comparison level is higher than a predetermined ratio. The comparison level is calculated to follows the detected level with a certain delay time when the detected concentration level increases at a rate exceeding a predetermined rate, so that the ratio of the detected level to the comparison level becomes sufficiently high. When it is determined that the gas concentration is high, operation of an automobile air conditioner is switched from an outside air mode to an inside air mode.

It is known that there are two regions in detecting the gas concentration, one is a stable region where the detected concentration level changes according to an actual concentration and the other is an unstable region where the detected level abruptly changes independently from the actual concentration. In the aforementioned detector, however, the gas concentration is detected without differentiating two regions. Accordingly, the detector cannot accurately detect the gas concentration in the, unstable region for the reason described below.

The detector includes a gas sensor composed of an oxide-semiconductor as a gas-sensitive element and a heater for heating the oxide-semiconductor. When the oxide-semiconductor is not heated, moisture and oxygen are chemically absorbed on its surface. When it is heated, moisture and oxygen are removed from the surface, thereby bringing the surface to a state where excessive electrons present on the surface. Oxygen adjacent to the surface is attracted by the electrons and absorbed to the surface (referred to as negative charge absorption), making a potential barrier between semiconductor molecules high and thereby increasing an electrical resistance of the oxide-semiconductor. Since the gas concentration is detected based on the resistance, the detected level increases. This creates the unstable region where the detected level rapidly increases independently from an actual concentration level. After the detected level reaches a certain level, the stable region appears, where the detected level changes according to the actual concentration level.

If the comparison level is set based on the operation in the stable region, commonly to the stable region and the unstable region, as is in the aforementioned conventional detector, the actual concentration level cannot be detected by comparing the detected level with the comparison level. That is, the ratio of the detected level to the comparison level exceeds a predetermined ratio, even when the actual concentration level is not high.

SUMMARY OF THE INVENTION

The present invention has been made in view of the above-mentioned problem, and an object of the present invention is to provide an improved gas concentration detector which is able to detect the actual gas concentration even in the unstable region.

The gas concentration detector of the present invention detects a concentration of pollutant gas such as NOx or SOx contained in ambient air. The detector is composed of an oxide-semiconductor gas sensor heated by an electric heater and a controller for determining the gas concentration based on a detected concentration level and a calculated comparison level. The controller includes a microcomputer, a timer and other components. The oxide-semiconductor gas sensor absorbs moisture when it is not heated. Until the gas sensor is sufficiently heated to remove the absorbed moisture and the oxygen attraction by negative charges is saturated, there is an unstable region where the gas concentration is not correctly detected. After that, the gas sensor enters a stable region where the gas concentration is correctly detected.

The controller calculates a comparison level with which the detected level is compared to determine the gas concentration. The comparison level is calculated so that it follows the detected level with a certain delay. When a ratio of the detected level to the comparison level becomes higher than a certain value, or when a difference between the two levels exceeds a predetermined value, the detector determines that the gas concentration is high. Though the gas concentration is correctly determined in this manner in the stable region, it cannot be determined in the unstable region. To make it possible to determine the gas concentration in the unstable region, the delay of the comparison level to the detected level is made smaller than the delay in the stable region, thereby making the comparison level quickly follows the detected level.

The gas sensor periodically outputs the detected level with a certain interval, and the controller calculates the comparison level with the same interval. A present comparison level $Bgs(n)$ is calculated according to the following formula: $Bgs(n)=Bgs(n-1)+[Vgs(n)-Bgs(n-1)]/m$, where $Bgs(n-1)$ is a previous comparison level, $Vgs(n)$ is a present detected level and m is a time constant larger than one. Accordingly, the delay in the unstable region can be made smaller by making time constant m smaller compared with that in the stable region.

The gas concentration detector may be used in an automobile air conditioner operated under an inside air mode or an outside air mode. When the detector determines that the pollutant gas concentration in the outside air is high, the air conditioner operation is switched from the outside air mode to the inside air mode.

To determine the duration of the unstable region, a heater-operated time for supplying heat to the oxide-semiconductor gas sensor is measured by the timer in the controller. Further, to estimate an amount of moisture absorbed to the oxide-semiconductor gas sensor while the sensor is not energized, the non-energized time may be measured by the timer. The time constant m is set according to the non-energized time, so that the comparison level follows the detected level more quickly when a higher amount of moisture is estimated to be absorbed.

According to the present invention, the gas concentration in ambient air is effectively determined even in the unstable region of the oxide-semiconductor gas sensor.

Other objects and features of the present invention will become more readily apparent from a better understanding of the preferred embodiments described below with reference to the following drawings.

DETAILED DESCRIPTION OF THE PREFERRED EMBODIMENTS

A first embodiment of the present invention will be described with reference to FIGS. 1–5. The gas concentration detector is used in an automobile air conditioner to automatically set its operation either to an inside air mode or an outside air mode based on an output of the gas concentration detector.

Figure 1:
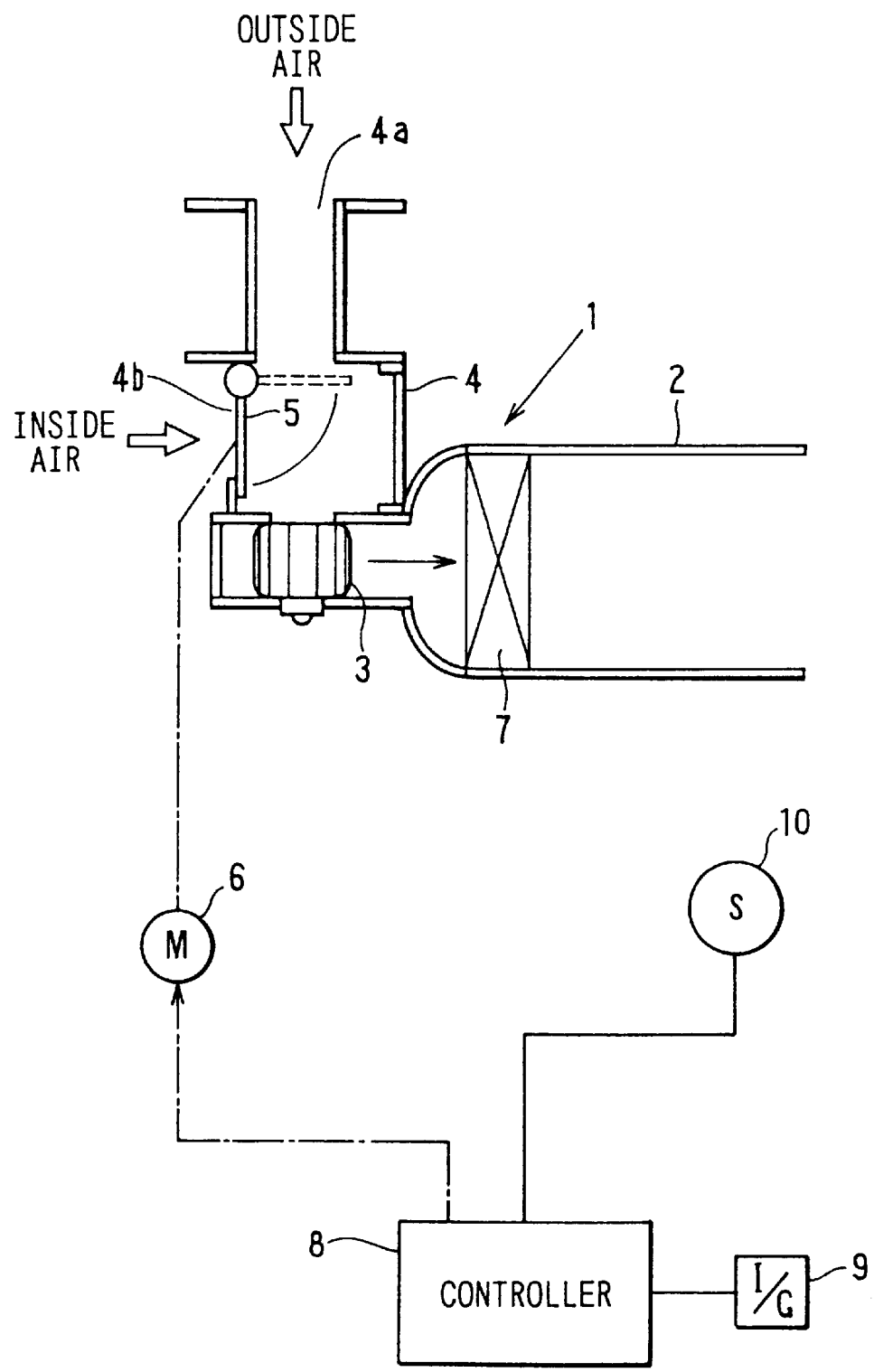
FIG. 1 is a drawing schematically showing a structure of an automobile air conditioner in which a gas concentration detector of the present invention is used.

FIG. 1 briefly shows an entire structure of the automobile air conditioner. An air conditioner unit 1 is composed of a case 2, a blower 3, a mode-switching box 4, a switching door 5, a serbomotor 6 and other components. The switching door 5 disposed in the mode-switching box 4 is driven by the serbomotor 6. The serbomotor 6 is controlled by a controller 8 to which a gas sensor 10 and an ignition switch 9 are connected.

Air outside an automobile compartment is introduced into the air conditioner unit 1 through an outside air inlet port 4a disposed upstream of the blower 3. Air inside the compartment is introduced through an inside air inlet port 4b also disposed upstream of the blower 3. An evaporator 7, a component of a conventional cooling system, is disposed in the case 2, and other air conditioner components (not shown) such as a heater core and an air mix door are disposed downstream of the evaporator 7. The outside air or the inside air introduced into the air conditioner unit 1 is blown toward the evaporator 7 that cools down the introduced air. The cooled air and heated air by the heater (not shown) are mixed to obtain a desired temperature, and then the mixed air is blown into a passenger compartment through the case 2.

The serbomotor 6 drives the switching door 5 to selective open the outside air inlet port 4a or the inside air inlet port 4b. The controller 8 controls the serbomotor 6 based on the output signal from the gas sensor 10 that detects pollutant gas (such as NOx) concentration in the outside air. The gas sensor 10 is mounted on the automobile at a position where the outside air is sufficiently blown to the gas sensor 10, e.g., at a front grill covering a radiator. Thus, the outside air is introduced into the air conditioner unit 1 when the gas concentration in the outside air is not high and the inside air is introduced when the gas concentration in the outside air is high.

The controller 8 includes a known microcomputer (not shown) composed of CPU, RAM, ROM and other components; A/D converter circuits; timer circuits and so on. Upon closing the ignition switch 9, electric power is supplied to the controller 8 from an on-board battery (not shown) The output signal from the gas sensor 10 that detects NOx concentration in the outside air is fed to the controller 8, and other switches (not shown) such as a switch for manually selecting operation modes of the air conditioner are also connected to the controller 8.

Figure 2:
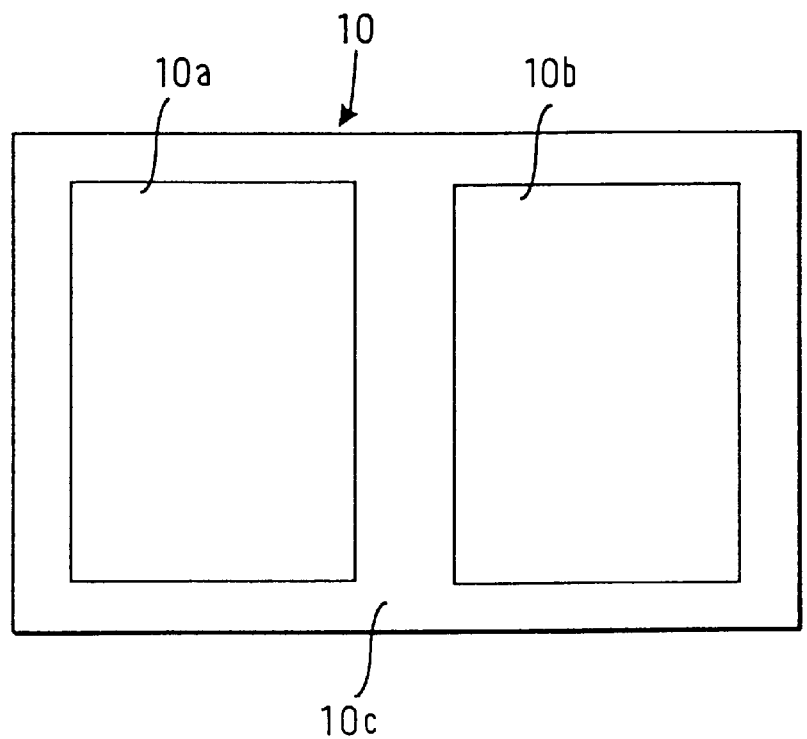
FIG. 2 is a schematic plan view showing a gas sensor used in the gas concentration detector of the present invention.

As shown in FIG. 2, the gas sensor 10 is composed of an oxide-semiconductor 10a (such as $SnO_2$) as a gas-sensitive element and an electric heater 10b for. heating the oxide-semiconductor 10a, both being mounted on an alumina substrate 10c. Upon closing the ignition switch 9, power is supplied to the oxide-semiconductor 10a and the heater 10b. The oxide-semiconductor 10a attracts oxygen and NOx gas to its surface when heated, and thereby its electrical resistance increases. The resistance value represents the detected NOx concentration. The oxide-semiconductor 10a is heated by the heater 10b to about 300° C.

Figure 10:
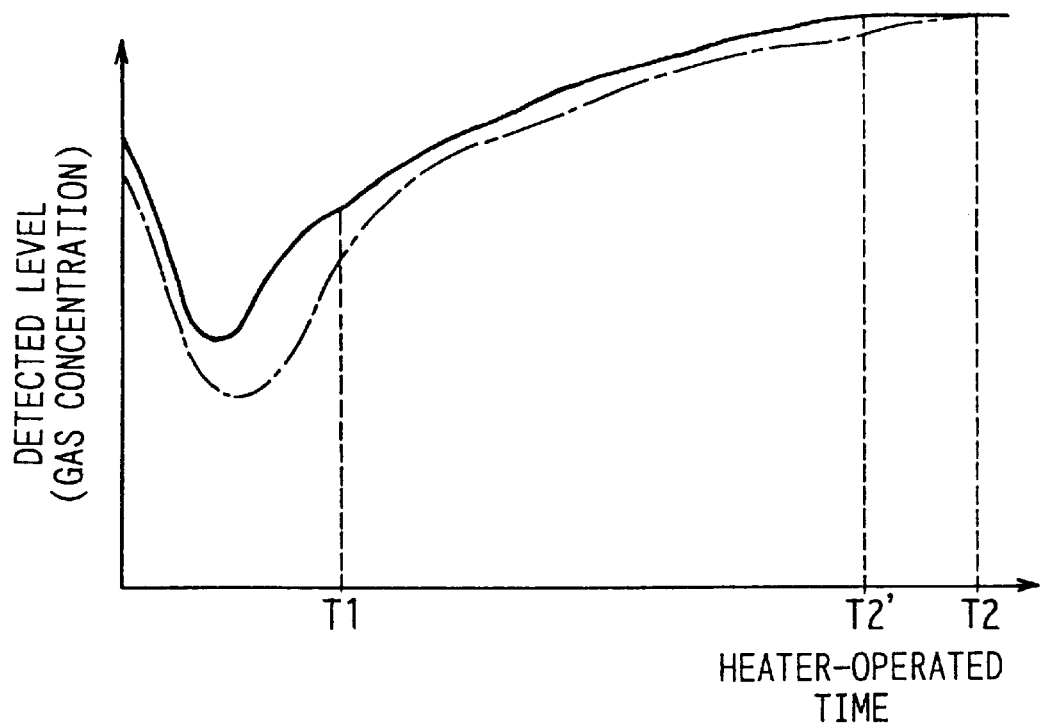
FIG. 10 is a graph showing a detected gas concentration level versus heater-operated time and showing a difference between a level detected when a large amount of moisture is absorbed to the gas sensor and another level detected when a small amount of water is absorbed to the gas sensor.

When the oxide-semiconductor 10a is not heated, it absorbs moisture as mentioned above. When the oxide-semiconductor 10a is heated, the detected gas concentration level represented by its resistance changes as shown in FIG. 10. More particularly, the detected level changes as shown by a chained line when a higher amount of moisture is absorbed, while it changes as shown by a solid line when a less amount of moisture is absorbed. Both curves sharply drops and rises up again during a period from switching-on of the heater 10b to a time T1 (a first predetermined time), and then the unstable region described above follows. The unstable region continues from T1 to T2 (a second predetermined time) in the case where a higher amount of moisture is absorbed, while it continues form T1 to T2' in the case where less moisture is absorbed. In other words, the unstable region is longer when much moisture is absorbed, and it is shorter when less moisture is absorbed. The stable region in which detected level changes according to the actual concentration level follows the unstable region.

Figure 4:
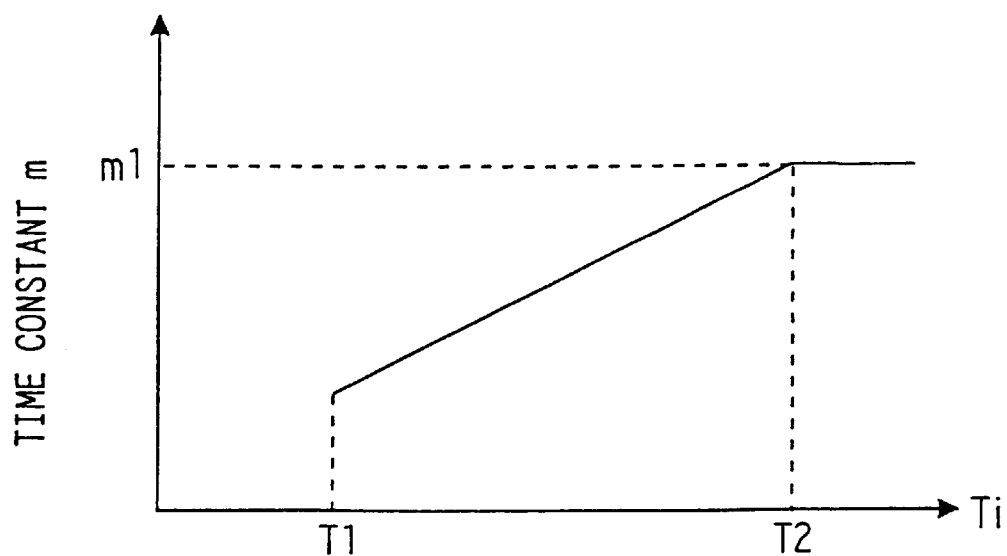
FIG. 4 is a graph showing a time constant m versus heater-operated time.
Figure 3:
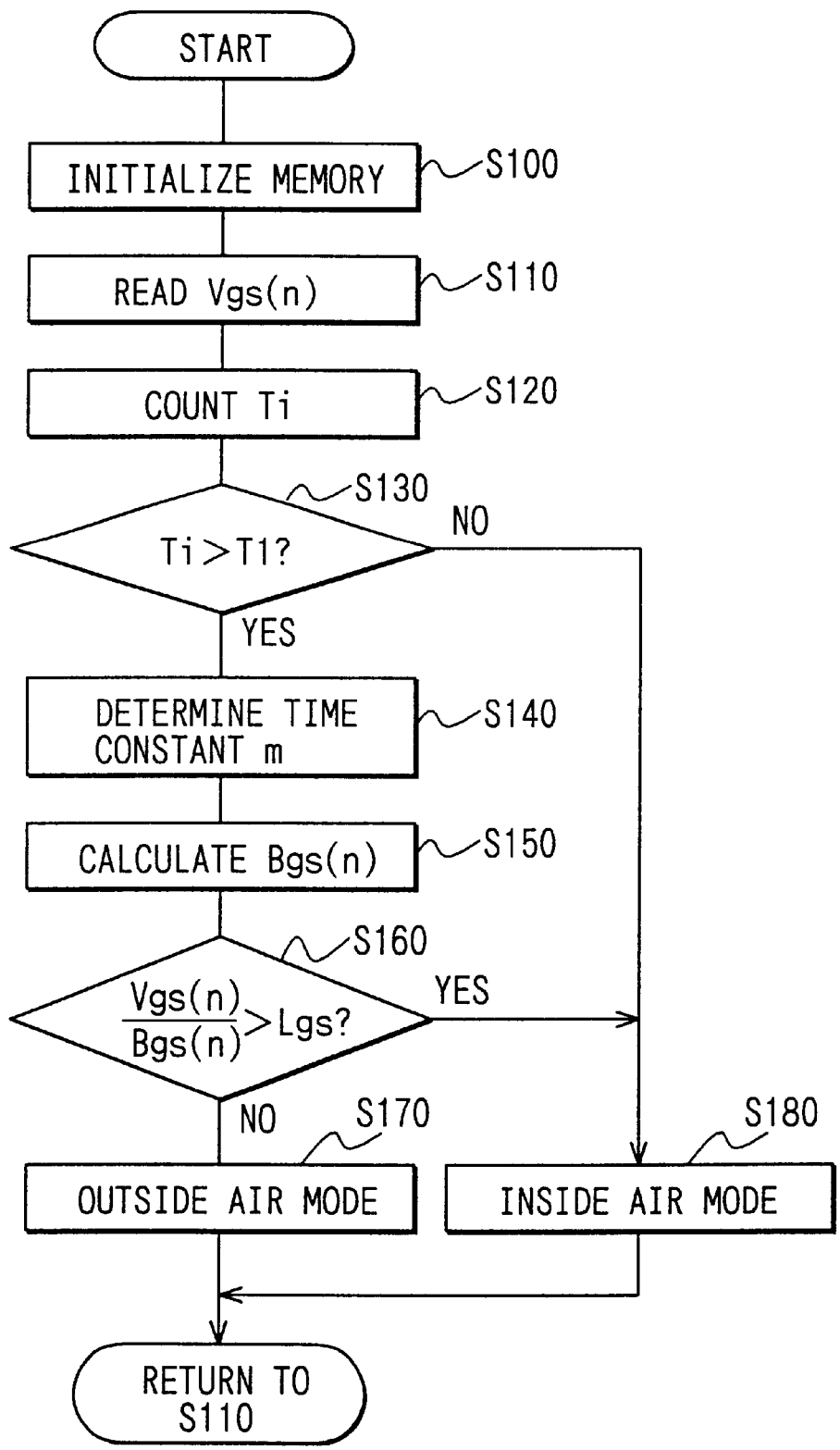
FIG. 3 is a flowchart showing a process of setting a operation mode of an automobile air conditioner either to an inside air mode or an outside air mode based on an output of the gas concentration detector.
Figure 5:
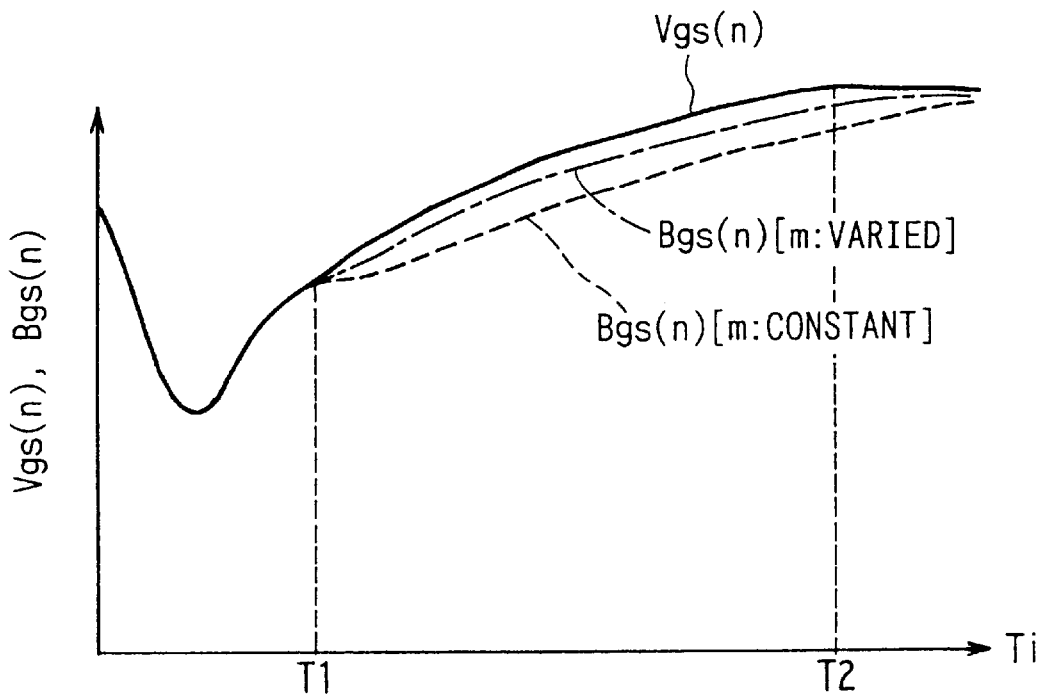
FIG. 5 is a graph showing a detected level and a comparison level versus heater-operated time.

Now, a process of controlling the switching door 5, as a first embodiment of the present invention, will be described with reference to FIGS. 3–5. The process routine shown in FIG. 3 is periodically performed with predetermined intervals when the air conditioner is set to an automatic mode in which its operation is automatically switched from the inside air mode to the outside air mode, or vice versa. When the air conditioner is set to either the inside air mode or the outside air mode, the process routine is not performed.

Referring to FIG. 3, upon starting the process, electric power is supplied to the oxide-semiconductor 10a and the heater 10b (referred to as energization of the gas sensor 10). Then, at step S100, a timer and a memory in the computer are initialized. At step S110, a gas concentration level Vgs(n) detected at that time (n) is read. At step S120, an enegization time Ti of the gas sensor 10 is counted by the timer from the beginning of enegization. At step S130, it is determined whether Ti is longer than a first predetermined time T1. During a period of time 0 to T1, the variation rate of the detected level Vgs(n) is too high to follow even if a delay time of the comparison level Bgs(n) is made short, as explained below. Therefore, the automatic mode control is not effected during this period of time (0 to T1), and the control mode is fixed to the inside air mode.

If it is determined at step S130 that the energization time Ti is longer than the first predetermined time T1 (Ti>T1), the process moves to step S140. If not, the process moves to S180. At step 140, a time constant m is determined according to the enegization time Ti, based on a map shown in FIG. 4. More particularly, the time constant m is set to m1 at a second predetermined time T2 and thereafter, and is set to linearly increase from a certain level to m1 during the period of T1 to T2. The detection of gas concentration during the period 0 to T2 is unstable, and the gas concentration is stably detected after the second predetermined time T2 (the stable region) The time constant m1 is set to a value, so that NOx concentration is properly determined in the stable region according to a formula explained below.

At step S150, a comparison level Bgs(n) at this time is calculated according to the following formula and memorized in a memory:

$$Bgs(n)=Bgs(n-1)+[Vgs(n)-Bgs(n-1)]/m,$$

where Bgs(n−1) is a comparison level at a previous time, Vgs(n) is a detected level at this time, and m is a time constant determined at step S140. An initial level of Bgs(n−1) is set to a level equal to Vgs(n). Bgs(n) at present thus calculated and memorized is used as a previous comparison level in calculating the next comparison level Bgs(n+1). As seen in the foregoing formula, the smaller the time constant m is, the higher value is added to the previous comparison level Bgs(n−1) in calculating the present comparison level Bgs(n). This means that the comparison level Bgs(n) follows the detected value Vgs(n) with a smaller delay as the time constant m becomes smaller. FIG. 5 shows how the detected level Vgs(n) and the comparison level Bgs(n) vary versus the energization time of the sensor 10. The solid line shows the detected level Vgs(n), the dotted line shows the comparison level Bgs(n) when the time constant m is fixed, and the chained line shows the comparison level Bgs(n) when the time constant m is varied according to the graph shown in FIG. 4. It is seen that the delay of the comparison level Bgs(n) is smaller when the time constant m is varied, compared with that when m is fixed.

At step S160, a ratio of the detected level Vgs(n) to the comparison level Bgs(n) is calculated and compared with a predetermined value Lgs. If the ratio, Vgs(n)/Bgs(n), is larger than Lgs, the process proceeds to step S180, and if not, it proceeds to step S170. At step S180, the air conditioner control is switched to the inside air mode. At step S170, the air conditioner control is switched to the outside air mode. Then, the process returns to step S110, and thereafter the same steps S110–S180 are periodically repeated.

Since, in the first embodiment described above, the comparison level Bgs(n) follows the detected level Vgs(n) with a smaller delay by setting the time constant m smaller in the unstable region than in the stable region, the detected level Vgs(n) can be effectively compared with the comparison level Bgs(n) to determine the actual NOx concentration even in the unstable region.

A second embodiment of the present invention will be described with reference to FIGS. 6 and 7. In this embodiment, only the step S140 for determining the time constant m in the first embodiment is replaced with steps S141–S143, and other steps are the same as those of the first embodiment. In the second embodiment, power is supplied to the controller 8 so that the timer therein can count a period of time $T_{off}$ in which the gas sensor 10 has not been energized and the heater 10b has not. operated before the routine shown in FIG. 3 starts.

Figure 6:
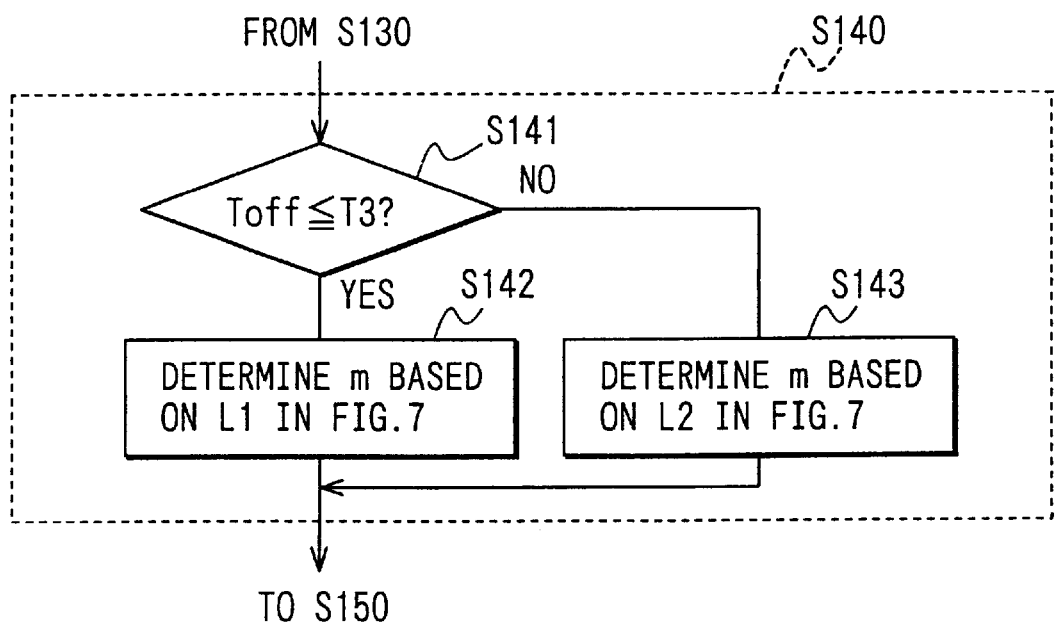
FIG. 6 is a flowchart showing a modified part of the process shown in FIG. 3 as a second embodiment.
Figure 7:
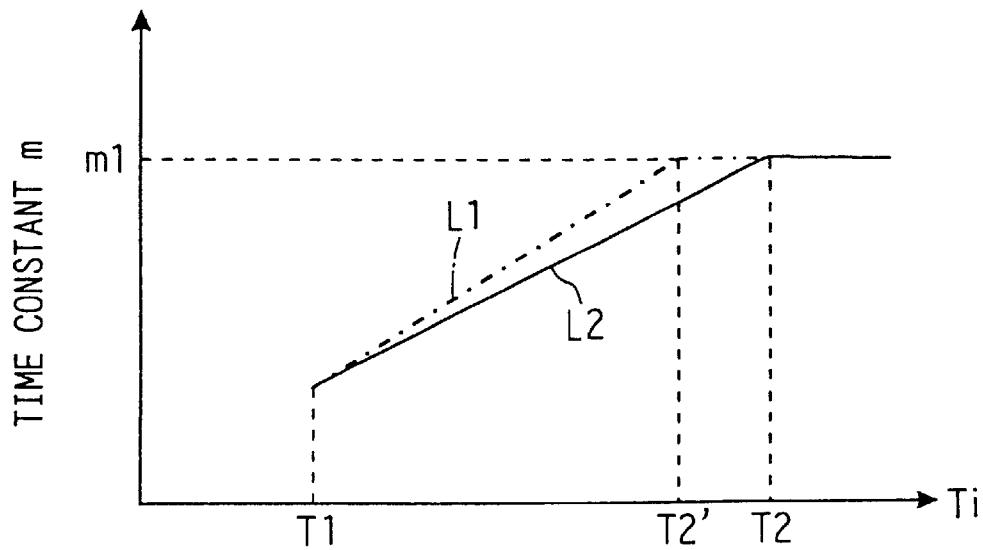
FIG. 7 is a graph showing a time constant m for the second embodiment versus heater-operated time.

Referring to FIG. 6, whether the time $T_{off}$ is equal to or shorter than a third predetermine time T3 is determined at step S141. If $T_{off} \leq T3$, the process proceeds to step S142 where the time constant m is determine based on line L1 shown in FIG. 7. If $T_{off}$ is longer than T3, the process proceeds to step S143 where the time constant is determined based on line L2 shown in FIG. 7. Then, the process proceeds to step S150. In other words, $T_{off}$ is equal to or shorter than the third predetermined time T3, the second predetermined time T2 is shortened to T2' thereby to set the time constant m higher than the time constant which is set when $T_{off}$ is longer than T3.

As described above with reference to FIG. 10, the unstable region becomes larger when the higher amount of moisture is absorbed on the surface of the oxide-semiconductor 10a. When the heater 10b is not operated for a long time, a high amount of moisture is absorbed. That is, the amount of moisture absorbed can be represented by the time Toff during which the heater is not operated. Therefore, in this embodiment, $T_{off}$ is counted by the timer, and the time constant m is calculated according to $T_{off}$. As seen in the graph of FIG. 7, the second predetermined time T2' is set shorter than T2 when $T_{off}$ is short, thereby to properly calculate the time constant m. In other words, if much moisture is absorbed by not operating the heater for a long time, the time constant m is set lower so that the comparison level Bgs(n) follows the detected level Vgs(n) with a less delay. Accordingly, NOx concentration is properly detected, not depending on the heater-off time $T_{off}$.

Figure 8:
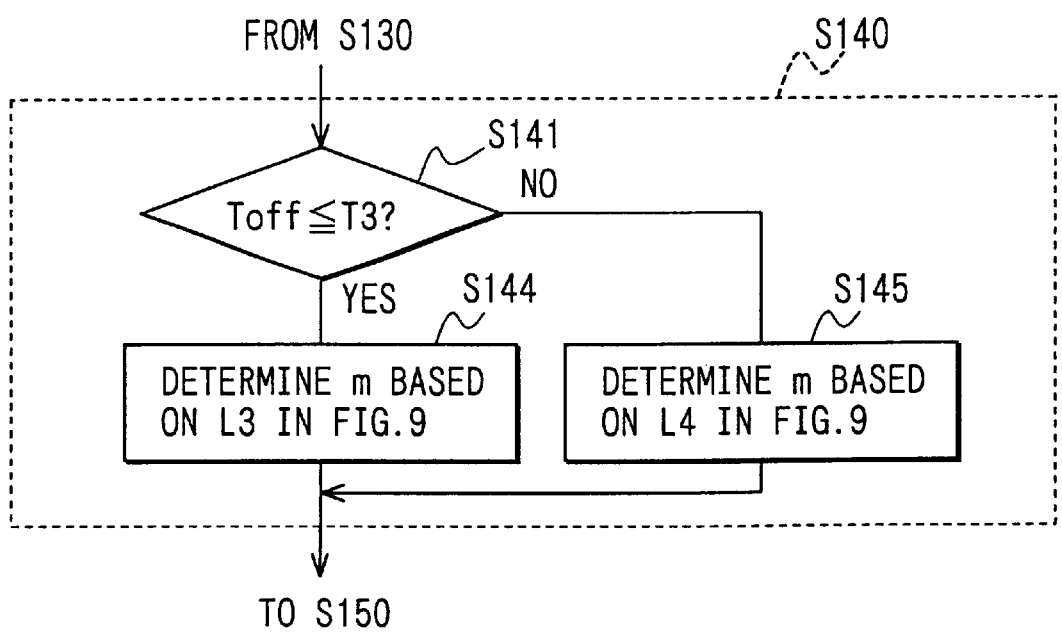
FIG. 8 is a flowchart showing another modified part of the process shown in FIG. 3 as a third embodiment.
Figure 9:
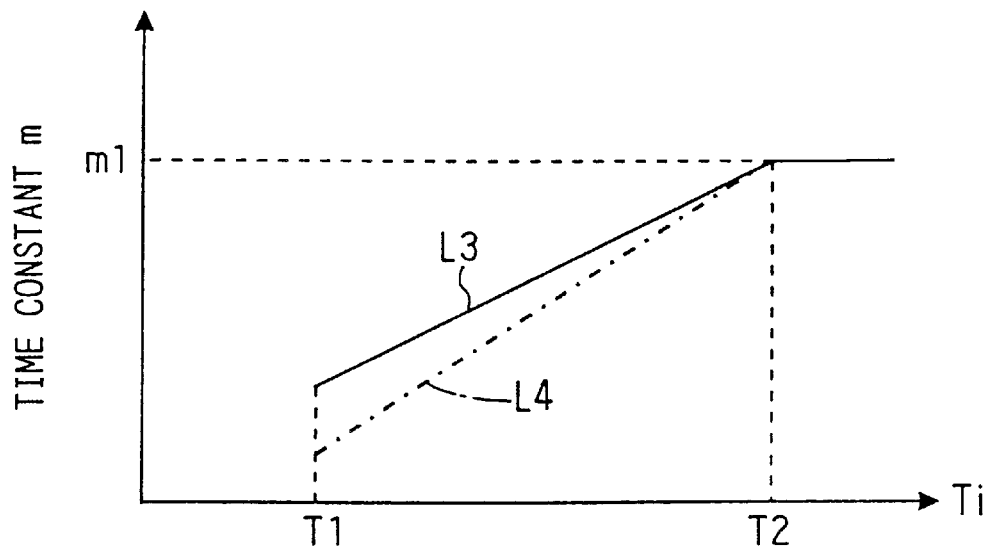
FIG. 9 is a graph showing a time constant m for the third embodiment versus heater-operated time.

A third embodiment of the present invention will be described with reference to FIGS. 8 and 9. In this embodiment, only the step S140 shown in FIG. 3 is replaced with steps S141, S144 and S145 shown in FIG. 8, and the time constant m is calculated according to the graph shown in FIG. 9. Referring to FIG. 8, whether $T_{off}$ is equal to or shorter than T3 is determined at step S141 in the same manner as in the second embodiment. The third predetermined time T3 is set to 24 hours in this embodiment. If $T_{off} \leq T3$, the process proceeds to step S144, and if $T_{off} > T3$, the process proceeds to step S145. At step S144, the time constant m is calculated based on line L3 shown in FIG. 9. At step S145, the time constant m is calculated based on line L4 shown in FIG. 9. In other words, the time constant m in the unstable region is calculated, so that it becomes smaller when $T_{off}$ is long than when $T_{off}$ is short. Since the time constant m is adequately calculated according to $T_{off}$ and Ti in the unstable region in this embodiment, the NOx concentration is surely detected even in the unstable region.

Though the operation mode of the air conditioner is switched between the inside air mode and the outside air mode based on the gas concentration detected by the gas concentration detector in the embodiments described above, it is also possible to control an air purifier based on the detected gas concentration. The air purifier may be operated when the gas concentration is found to be high and turned off when the gas concentration is low. Though the NOx concentration is detected in the embodiments described above, the concentration of other pollutant gases such as Sox may be detected in the same manner. Though the gas concentration is detected based on the ratio of the detected level to the comparison level (Vgs(n)/Bgs(n)) in the foregoing embodiments, it is also possible to detect the gas concentration based on a difference between the detected level and the comparison level (Vgs(n)−Bgs(n)).

Though the oxide-semiconductor 10a is heated by the electric heater 10b mounted on the same substrate in the foregoing embodiments, other heaters disposed separately from the oxide-semiconductor 10a may be used for the same purpose to heat the oxide-semiconductor. Though the time constant m is calculated so that it linearly varies in the period between T1 and T2, the time constant m in this period may be calculated in other manners or may be set to a fixed value less than m1, as long as the comparison level Bgs(n) follows more quickly the detected level Vgs(n) in the unstable region than in the stable region. Though the first predetermined time T1 is always fixed to a certain value in the foregoing embodiments, it may be varied according to $T_{off}$ in the similar manner as T2 is varied according to $T_{off}$ in the second embodiment. Further, it is also possible to design a control process by combining those of the second embodiment and the third embodiment.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A gas concentration detector for detecting a pollutant gas concentration, comprising:
    an oxide-semiconductor gas sensor operable to detect a gas concentration and output a detected level of the gas concentration, the gas sensor having a stable region where the detected level changes in proportion to the gas concentration and an unstable region where changes in the detected level are not proportional to changes in the gas concentration;
    heater for supplying heat to the gas sensor;
    means for calculating a comparison level that follows the detected level with a delay; and
    means for determining that the gas concentration is high when a ratio of the detected level to the comparison level or a difference between both levels exceeds a predetermined value, wherein:
        the calculating means calculates the comparison level so that the delay is smaller in the unstable region as compared with that in the stable region.

2. The gas concentration detector as in claim 1, further including a memory, wherein:
    the gas sensor periodically outputs a present value of the detected level with predetermined intervals;
    the calculating means periodically calculates a present value of the comparison level with the same intervals as the gas sensor;
    the memory memorizes each present value of the detected level and each present value of the comparison level; and
    the present value of the comparison level is calculated by adding a value less than a difference between the present value of the detected level and an immediately previous value of the comparison level to an immediately previous value of the comparison level.

3. The gas concentration detector as in claim 1, further including means for counting a heater-operated time during which the heater supplies heat to the oxide-semiconductor, wherein:
    the calculating means calculates the comparison level so that the delay becomes smaller before the heater-operated time reaches a predetermined time than after the heater-operated time exceeds the predetermined time.

4. The gas concentration detector as in claim 3, further including means for detecting an amount of moisture absorbed on an surface of the oxide-semiconductor, wherein:
    the predetermined time is set according to the amount of moisture absorbed.

5. The gas concentration detector as in claim 4, wherein:
    the calculating means calculates the comparison level to make the delay in the unstable region small when the detected amount of moisture is large.

6. The gas concentration detector as in claim 4, wherein:
    the means for detecting an amount of moisture absorbed is a timer that counts a period of time during which the heater is not operated.

7. The gas concentration detector as in claim 4, wherein:
    the predetermined time is set to a first level when the detected amount of moisture exceeds a predetermined amount and is set to a second level which is shorter than the first level when the detected amount of moisture is less than the predetermined amount.

8. The gas concentration detector as in claim 1, further including means for detecting an amount of moisture absorbed on an surface of the oxide-semiconductor, wherein:
    the calculating means calculates the comparison level to make the delay in the unstable region small when the detected amount of moisture is large.

9. The gas concentration detector as in claim 8, wherein:
    the means for detecting an amount of moisture absorbed is a timer that counts a period of time during which the heater is not operated.

10. The gas concentration detector as in claim 1, wherein:
    the oxide-semiconductor gas sensor is a sensor for sensing NOx concentration.

11. The gas concentration detector as in claim 1, wherein:
    the gas concentration detector is used in an automobile air conditioner operated by introducing air inside the automobile or by introducing air outside the automobile; and
    the inside air is introduced when the gas concentration detector determines that the gas concentration in the outside air is high, and the outside air is introduced otherwise.

12. The gas concentration detector as in claim 11, wherein:
    the gas sensor is mounted on a front grill of the automobile, so that the gas sensor is sufficiently exposed to the outside air.

* * * * *